US009625493B2

(12) United States Patent
Liu et al.

(10) Patent No.: US 9,625,493 B2
(45) Date of Patent: Apr. 18, 2017

(54) PROCESS CONTROL MONITORING FOR BIOCHIPS

(71) Applicant: Taiwan Semiconductor Manufacturing Company, Ltd., Hsin-Chu (TW)

(72) Inventors: Yi-Shao Liu, Zhubei (TW); Chun-Ren Cheng, Hsin-Chu (TW); Chun-Wen Cheng, Zhubei (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 991 days.

(21) Appl. No.: 13/774,708

(22) Filed: Feb. 22, 2013

(65) Prior Publication Data

US 2014/0239986 A1 Aug. 28, 2014

(51) Int. Cl.
*G01R 31/00* (2006.01)
*G01R 1/073* (2006.01)
(Continued)

(52) U.S. Cl.
CPC ..... *G01R 1/07307* (2013.01); *G01N 27/4145* (2013.01); *G01N 27/4163* (2013.01);
(Continued)

(58) Field of Classification Search
CPC .... G01K 7/16; G01R 33/302; G01R 33/3456; G01R 33/448; H01L 2924/14;
(Continued)

(56) References Cited

U.S. PATENT DOCUMENTS 5,334,931 A * 8/1994 Clarke ................... G01R 1/067
324/755.07
7,833,708 B2 * 11/2010 Enzelberger ............ B01F 5/102
435/287.2

(Continued)

OTHER PUBLICATIONS

Thanu, et al., "Post Plasma Etch Residue Removal in Dilute HF Solutions," ECS, J. Electrochem. Soc., http://jes.ecsdl.org/subscriptions, 2011, vol. 158, No. 8, pp. H814-H882.

*Primary Examiner* — Melissa Koval
*Assistant Examiner* — Trung Nguyen
(74) *Attorney, Agent, or Firm* — Slater Matsil, LLP

(57) ABSTRACT

The present disclosure provides a biosensor device wafer testing and processing methods, system and apparatus. The biosensor device wafer includes device areas separated by scribe lines. A number of test areas that allow fluidic electrical testing are embedded in scribe lines or in device areas. An integrated electro-microfluidic probe card includes a fluidic mount that may be transparent, a microfluidic channels in the fluidic mount in a testing portion, at least one microfluidic probe and a number of electronic probe tips at the bottom of the fluidic mount, fluidic and electronic input and output ports on the sides of the fluidic mount, and at least one handle lug on the fluidic mount. The method includes aligning a wafer, mounting the integrated electro-microfluidic probe card, flowing one or more test fluids in series, and measuring and analyzing electrical properties to determine process qualities and an acceptance level of the wafer.

21 Claims, 5 Drawing Sheets

(51) Int. Cl.
*G01N 27/414* (2006.01)
*G01N 27/416* (2006.01)
*G01R 1/067* (2006.01)

(52) U.S. Cl.
CPC .............. *B01J 2219/00531* (2013.01); *B01J 2219/00653* (2013.01); *B01J 2219/00659* (2013.01); *B01J 2219/00693* (2013.01); *G01R 1/06783* (2013.01)

(58) Field of Classification Search
CPC .... H01L 2924/00014; H01L 31/02019; G01N 2333/4745
USPC .. 324/500, 750.01, 522–531, 306, 353, 204, 324/750.08; 204/403.01; 205/782, 792
See application file for complete search history.

(56) References Cited

U.S. PATENT DOCUMENTS

| | | | |
|---|---|---|---|
| 8,471,559 B2* | 6/2013 | Taherian | G01N 24/081 324/303 |
| 2002/0149369 A1* | 10/2002 | Peck | G01R 33/302 324/321 |
| 2007/0249091 A1* | 10/2007 | Pan | B81C 1/00293 438/107 |
| 2011/0227558 A1* | 9/2011 | Mannion | G01N 33/48721 324/71.1 |
| 2013/0231453 A1* | 9/2013 | Chang | C08G 69/44 528/190 |
| 2014/0227147 A1* | 8/2014 | Beyer | B81C 1/00119 422/502 |

\* cited by examiner

PROCESS CONTROL MONITORING FOR BIOCHIPS

CROSS-REFERENCE TO RELATED APPLICATIONS

This application relates to the following co-pending and commonly assigned patent applications: Ser. No. 13/673,602, titled "Integrated Electro-Microfluidic Probe Card, System and Method for Using the Same," filed Nov. 9, 2012, which applications are hereby incorporated herein by reference.

FIELD

This disclosure relates to methods for forming and for testing biochips. Particularly, this disclosure relates to systems and methods for testing fabricated or partially fabricated biosensors on a wafer.

BACKGROUND

Biosensors are devices for sensing and detecting biomolecules and operate on the basis of electronic, electrochemical, optical, and mechanical detection principles. Biosensors that include transistors are sensors that electrically sense charges, photons, and/or mechanical properties of bio-entities or biomolecules. The detection can be performed by detecting the bio-entities or biomolecules themselves, or through interaction and reaction between specified reactants and bio-entities/biomolecules. Biosensors include BioFETs (biological field-effect transistors, biologically sensitive field-effect transistors, biologically active field-effect transistors, or bio-organic field-effect transistors), optical sensors (for example, a CMOS image sensor), electrochemical biosensors, and mass sensitive sensors (for example, with embedded piezoelectric crystals). Such biosensors can be manufactured using semiconductor processes, can quickly convert biomolecular information to electric signals, and can be easily applied to integrated circuits (ICs) and microelectromechanical systems (MEMS).

Biochips are essentially miniaturized laboratories that can perform hundreds or hundreds thousands of simultaneous biochemical reactions. Biochips can detect particular biomolecules, measure their properties, process resulting signals, and may even analyze the data directly. Biochips enable researchers to quickly screen large numbers of biological analytes for a variety of purposes, from disease diagnosis to detection of bioterrorism agents. Advanced biochips use a number of biosensors along with fluidic channels to integrate reaction, sensing and sample management. While biochips are advantageous in many respects, challenges in their fabrication and/or operation arise, for example, due to compatibility issues between the semiconductor fabrication processes, the biological applications, and restrictions and/or limits on the semiconductor fabrication processes.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
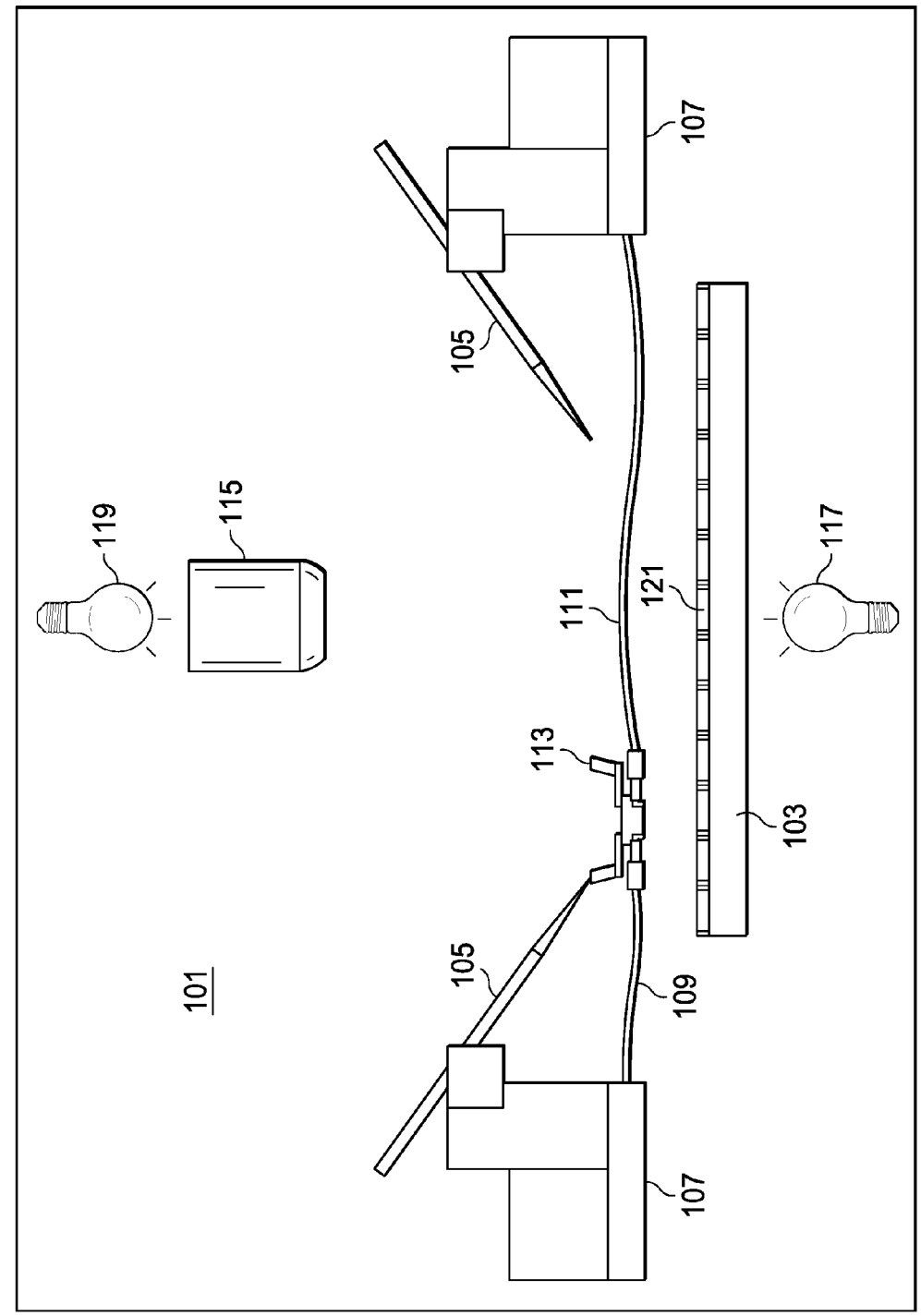
FIG. 1 is a schematic of a wafer-level biosensor testing tool according to various embodiments of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

A simple conventional biochip involves various bioreceptors which react with various biological material of interest in one or more patterned sites. Various approaches are used to differentiate among different reactants and reactions for detection. One common approach is to tag a reaction with a fluorescent or phosphorescent bioreceptor that emits a detectible photon. A coordinated, or ordered array, approach would encode the sensor or bioreceptors to a location on the biochip, so that a positive reaction and photo-detection would be correlated to the location to determine the nature of the reaction, for example, identity of the biological material. In many cases, the location is externally observed by optical detection. In other cases, the location corresponds to an embedded sensor that signals a measurement. The signal may be optical, magnetic, electrical, or a mass-sensitive measurement such as surface acoustic wave or microbalance weights. Another approach is the random approach that encodes the sensor with different fluorescence, phosphorescence, or otherwise detectible and differentiable tags. A positive detection would be correlated to the type of signal transduced to determine the nature of the detection. The signal transduced may be photons, for example, a different wavelength light is generated for different biological materials or reactions, or surface plasmon resonance.

More advanced biochips involve not only biosensors, but also various fluidic channels to deliver biological material to the sensors. The fluidic channels may be a part of a microfluidic system that includes pumps, valves, and various measurement devices such as flow meters, pressure transducers, and temperature sensors. Because a biochip combines electrical processing and fluid processing, fluid handling ability has to successfully integrate within a semiconductor chip environment. A potential use of biochips is as a lab-on-a-chip where medical professionals can use a small biochip to perform testing in the field, obtain results contemporaneously, and proceed with treatment or further analysis without retreating to a laboratory. Especially for medical professionals working in remote areas where sample preservation may be difficult, lab-on-a-chip devices can save traveling and waiting time and costs. These lab-on-a-chip devices are often single-use, or disposable, devices. As such, the manufacturing costs have to be low to be economically viable.

A biochip may include a number of BioFETs and other transistors and circuitry. Each of the BioFETs has a sensing surface associated with a microfluidic channel or well where a biological matter may flow and be sensed. A biochip may be manufactured by several entities and assembly/testing may be performed by yet other entities. In a typical scenario, the transistors including BioFETs and non-bio FETs are manufactured on a semiconductor substrate in a semiconductor manufacturing fabrication facility using complementary metal-oxide-semiconductor (CMOS) process compatible techniques. In some instances, the microfluidic structures on the biochip are formed directly on the substrate after the transistors and circuits are formed. In other instances, the microfluidic structures on the biochip are formed separately and attached at the semiconductor manufacturing fabrication facility. In some instances, the microfluidic structures on the biochip are formed separately and attached at another facility, which may be a customer or a vendor of the semiconductor manufacturing fabrication facility.

A semiconductor manufacturing fabrication facility is equipped to perform chip level, wafer level, and wafer level chip scale testing for the semiconductor devices produced at the fabrication facility. A general semiconductor probe station usually includes micromanipulators or probe cards for electrical probing of a partially or fully fabricated device. If some defect criteria are met, the product may be reworked, marked, or discarded. While the basic electrical properties may be tested, the portions of the biochips used with biological fluids, such as sensing surfaces and microfluidic channels, cannot be tested using a traditional semiconductor probe station. Further, some biochips are designed to be single-use devices, testing of the biochip would render it unusable.

The present disclosure provides a method and system for wafer level chip scale post-processing and testing of biochips, such as a Lab-On-Chip device. The ability to verify functionality and yield of a wafer of biochip, thus be able to accept or reject a manufactured wafer, without shipping for testing to be performed at a customer site and resultant delaying make mass production of biochips in a semiconductor foundry economically viable. A wafer-level biosensor processing and testing tool can integrate post-processing (sensing surface functionalization, sample delivery) and testing (optical probing for fluidic dynamics and biological reactions; electrical probing for device characteristics and performances). The wafer-level biosensor testing tool can monitor the biological reactions via an attached microscope in real-time. The wafer-level biosensor testing tool allows testing and diagnostics/trouble shooting, if a problem is detected. The wafer-level biosensor testing tool also expedites feedback to the manufacturer of biochips. A wafer-level biosensor processing and testing tool is disclosed in U.S. patent application Ser. No. 13/673,602, titled "Integrated Electro-Microfluidic Probe Card, System And Method for Using The Same," filed Nov. 9, 2012, by inventors Liu et al., which is hereby incorporated by reference in its entirety for all purposes.

The present disclosure provides a testing method and a biosensor device wafer design that allows collection of wafer acceptance data using a wafer-level biosensor testing tool. The biosensor device wafer design results in efficient use of silicon real estate while collecting relevant performance data. One testing platform combines the various functions for electrical and biological testing.

FIG. 1 is a schematic of a wafer-level biosensor testing tool 100 according to various embodiments of the present disclosure. The wafer-level biosensor testing tool 100 may be enclosed in a chamber 101 to allow for environmental control. For example, the various processing and testing may be performed in a temperature or pressure environment different from the ambient. The chamber 101 may include gas inlets and outlets to control an atmospheric composition during processing and testing. For mass production, load locks and automated wafer carrier/cassette handling may also be incorporated into the wafer-level biosensor testing tool. According to some embodiment, a wafer-level biosensor testing tool chamber 101 includes a wafer stage 103, at least one manipulator arm 105 to manipulate an integrated electro-microfluidic probe and other probes, fluid supply and attachments 107 for inlet 109 and outlet 111 to the integrated electro-microfluidic probe 113, and optical detection 115 and light sources 117 and 119 for optical verification and result collection.

Figure 2:
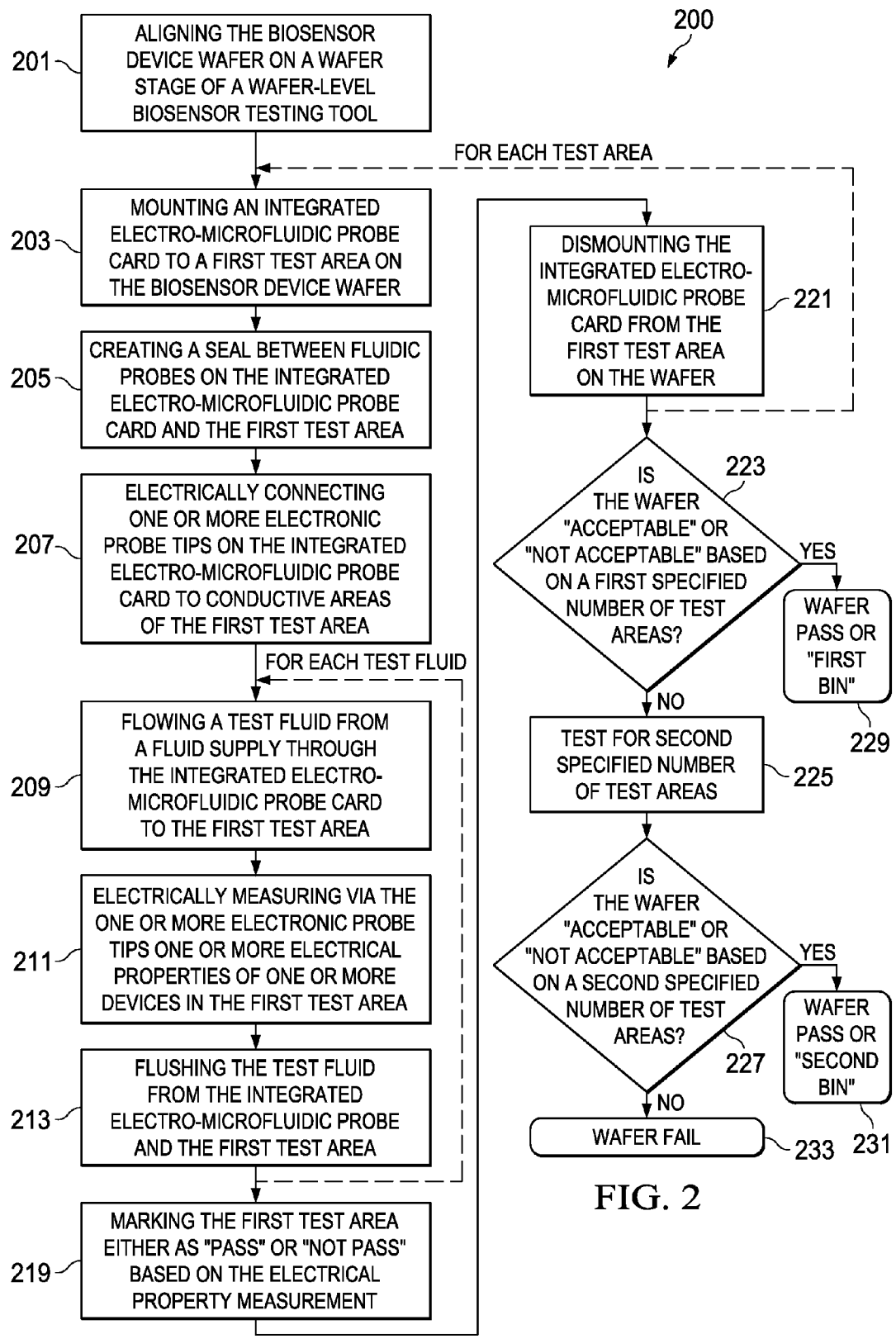
FIG. 2 is a flow chart of method embodiments of testing a biosensor device wafer according to one or more aspects of the present disclosure.

FIG. 2 is a flow chart of method embodiments 200 of testing a biosensor device wafer according to one or more aspects of the present disclosure. When a biosensor device wafer enters the wafer-level biosensor testing tool, the biosensors and sensing surfaces are already formed. In operation 201, a biosensor device wafer is positioned and aligned on a wafer stage in a wafer-level biosensor testing tool, which may be the wafer-level biosensor testing tool 100 of FIG. 1. In FIG. 1, the biosensor device wafer 121 may be positioned by a wafer transfer robot arm or the wafer may be manually placed by an operator. The wafer stage 103 may be at least partially transparent, to allow light from a light source 117 to transmit light through the wafer stage 103 during operation. The wafer stage 103 may be a pedestal, a susceptor, or a carousel where more than one wafer or workpiece may be processed or tested at the same time. The wafer stage may be moved in one or many directions to align the biosensor device wafer 121. According to various embodiments, the wafer stage 103 has freedom of motion in at least 2 directions: x and y. In some embodiments, the wafer stage 103 may be moved in 3 directions x, y, and z; x, z, and $\Theta$ (theta) (rotational); or x, y, and $\Theta$ (rotational).

In operation 203 of method 200 in FIG. 2, an integrated electro-microfluidic probe card is mounted to a first die and test area on the biosensor device wafer. In FIG. 1, the integrated electro-microfluidic probe card 113 includes a fluidic mount portion containing one or more fluidic probes and one or more electrical probes. The fluidic mount portion includes at least one set of fluid inlet and outlet that accepts test fluid or process fluid from a fluid supply, for example, fluid supply 107 via supply tube 109 and returns used fluid to via fluid return tube, for example, tube 111 to fluid return 107. The integrated electro-microfluidic probe card 113 includes one or more handle lugs attached to an edge portion or a side portion of the integrated electro-microfluidic probe card 113. The integrated electro-microfluidic probe card 113 is held and moved by one or more micromanipulator arms 105. During the operation, the micromanipulator arms 105 mounts the integrated electro-microfluidic probe by exerting downward pressure on the integrated electro-microfluidic probe card 113 so that the fluidic probe portion seals against the biosensor device wafer 121. Thus, the micromanipulator arm 105 is configured to move the integrated electro-microfluidic probe card 113 in at least a downward direction. According to various embodiments, the micromanipulator arms 105 have movable joints and/or a base capable of moving laterally as well as vertically. In some embodiments, the mounting operation includes the wafer stage moving up toward the integrated electro-microfluidic probe card 113.

Figure 3:
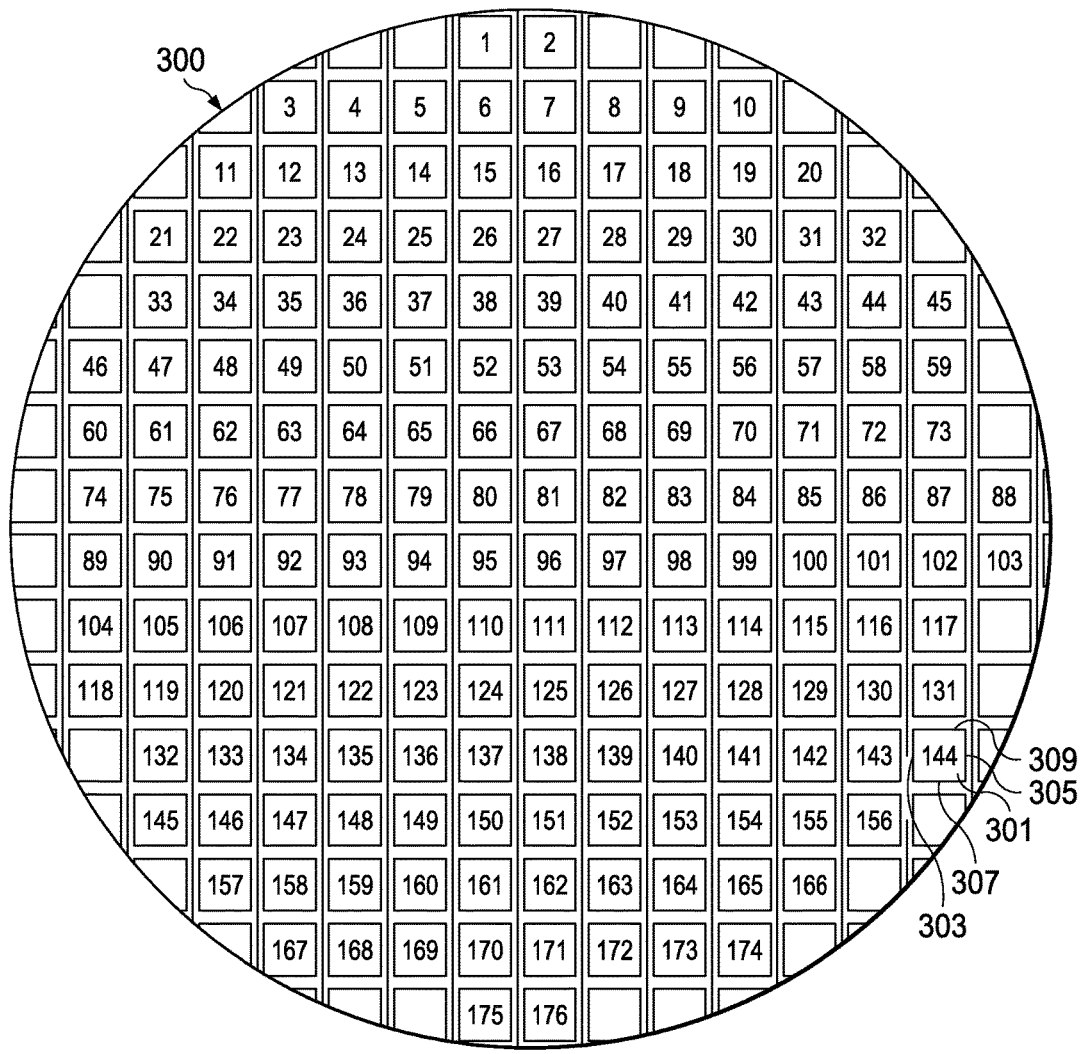
FIG. 3 is a schematic of biosensor device wafer according to one or more aspects of the present disclosure.

The integrated electro-microfluidic probe card is mounted to a first die and test area on the biosensor device wafer. The biosensor device wafer is manufactured with a number of test areas. Each test area is associated with a die location on the wafer. FIG. 3 is a schematic of biosensor device wafer 300 according to one or more aspects of the present disclosure. The biosensor device wafer 300 includes many dies. In various embodiments, the number of dies varies from few, such as 8 or 10, to many, such as many thousands or hundreds of thousands of small dies, for example, wafer 300 includes 176 active dies. The biosensor device wafer 300 is round; however, in some instances a biosensor device wafer with a flat portion or an alignment notch is used. Each die on a biosensor device wafer is separated from adjacent dies by a scribe line. For example, die 301 is surrounded by scribe lines 303, 305, 307, and 309. The test areas may be located in a scribe line region associated with a die or within the active region of a die.

Figure 4A:
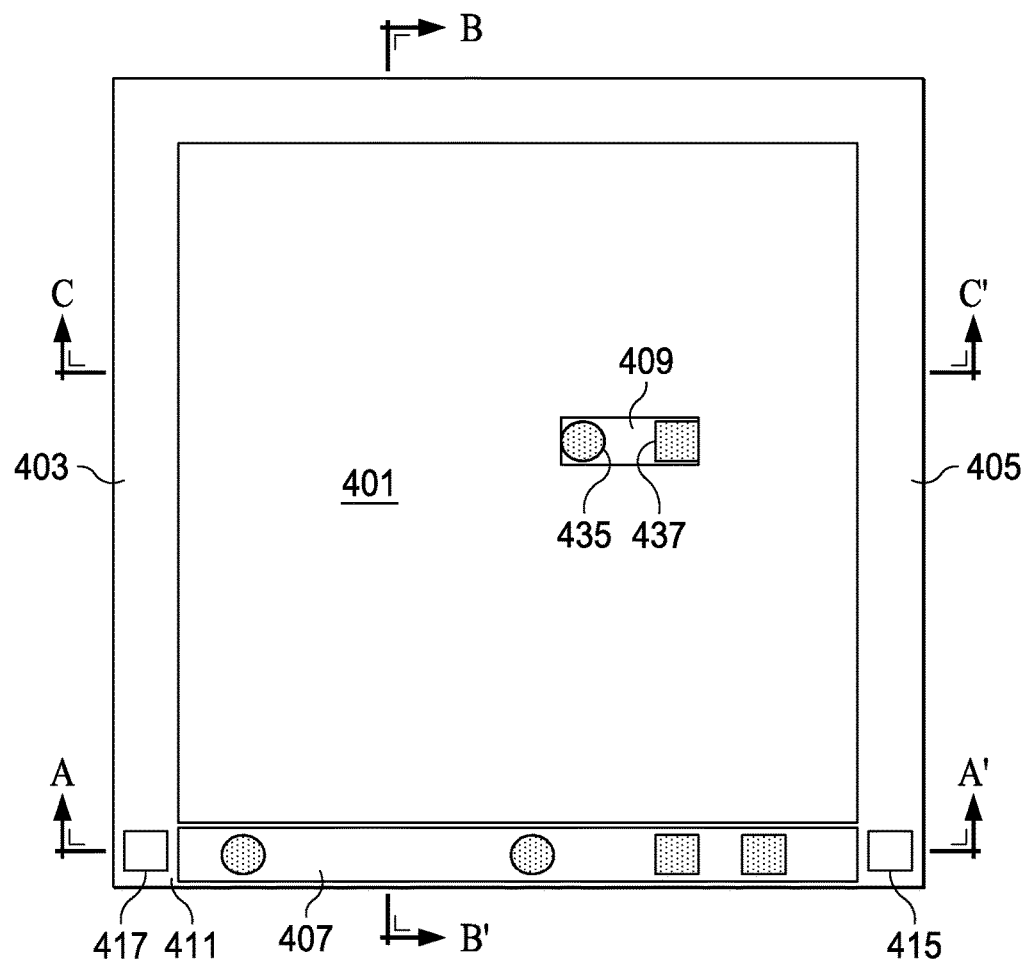
FIG. 4A is a biochip die and surrounding scribe line area in accordance with various embodiments of the present disclosure.

FIG. 4A is a biochip die and surrounding scribe line area in accordance with various embodiments of the present disclosure. FIG. 4A shows biochip die 401 with scribe lines 403 and 405 to either side and scribe line 407 below the biochip die 401. FIG. 4A also shows a test area 409 within the biochip die 401 and a test area 411 within the bottom scribe line 407. In some embodiments, more than one test area may be located within the biochip die 401. In some embodiments, all or some of the surrounding scribe lines may include test areas.

In operation 205 of method 200, a seal between fluidic probes on the integrated electro-microfluidic probe card and the first test area is created. The integrated electro-microfluidic probe card is designed to interface with one or more test areas associated with a die. For example, the integrated electro-microfluidic probe card seals against test area 411 of FIG. 4A for an active die on wafer 300 of FIG. 3. The fluidic probe on the integrated electro-microfluidic probe card includes conduits for conducting fluid to and from the test area 411. In order to create a seal, the portions of the integrated electro-microfluidic probe that interfaces with the test area may deform. However, the deformed portion is designed to return to their original shape after dismounting from the wafer so they may be re-used.

Figure 4B:
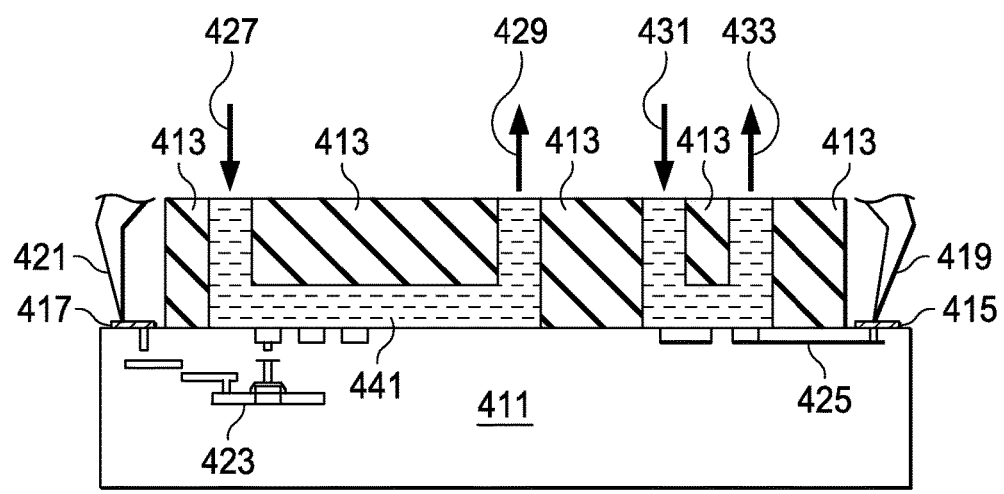
FIGS. 4B to 4E are cross-sectional views of the biochip of FIG. 4A with an integrated electro-microfluidic probe card mounted according to one or more aspects of the present disclosure.

In operation 207 of method 200, one or more electronic probe tips on the integrated electro-microfluidic probe card is electrically connected to conductive areas of the first test area. FIG. 4B shows a cross section of the test area 411 from sectional line A-A' of FIG. 4A and of the integrated electro-microfluidic probe card 413 mounted over it. As shown in FIGS. 4A and 4B, conductive areas 415 and 417 are electrodes in the scribe line areas electrically connected to the biosensors 423 and 425 in the test area 411. They are contacted by electronic probe tips 419 and 421 respectively on the integrated electro-microfluidic probe card 413 in operation 207. The various operations 203, 205, and 207 of mounting, forming a seal and electrical contacting may be performed at the same time when the integrated electro-microfluidic probe card is mated to the die and test area or be performed separately. For example, the electronic probes may be lowered onto the contacts 415 and 417 after a seal is formed to avoid fluid contamination of the probe tips. In another example, the mounting and the creating a seal may use different amount of pressure between the integrated electro-microfluidic probe card and the biosensor device wafer.

In operation 209, a test fluid is flowed from a fluid supply through the integrated electro-microfluidic probe card to the first test area. In some embodiments, the test fluid is flowed through one or more fluid inputs, e.g., fluid supply 107 and fluid tube 109 of FIG. 1. The test fluid may be de-ionized water or include a biological matter or a proxy for a biological matter to perform the test. The various flow mechanisms on the integrated electro-microfluidic probe card may pump and direct the test fluid toward one or more microfluidic wells or channels having the sensing surface. In FIG. 4B, the test fluid may enter the well at inlet 427 and exit at outlet 429 or enter the well at inlet 431 and exit at outlet 433.

In operation 211, one or more electrical properties of one or more biosensors in the first test area is electrically measured via the one or more electronic probe tips. The electrical properties of the biosensors in the test area are designed to correlate to the electrical properties of the biosensors in the active die 401. In other words, if the electrical property of the one or more biosensors in the test area is within a specified range using a test fluid, then the electrical property of the biosensors in the active die is also expected to be within a specified range. While the biosensors may be the same, for example, a BioFET in the test area and a BioFET in the active die, they need not be the same or to have exactly same specifications. Additionally, the electrical properties are obtained to determine the existence and amount of surface residue. By comparing impedance measurements against expected baselines where there is no residue, a surface residue amount can be estimated. Measurements may be further analyzed by numerical analysis with equivalent circuit models of the devices and electrodes. Information regarding specific surface property or device performance index could be thus extracted. The embodiments of FIG. 4B include a BioFET 423 and an impedance test electrodes 425. The BioFET 423 may include a front side sensing well or a back-side sensing surface. In other words, the side of the biosensor device wafer exposed to the integrated electro-microfluidic probe card may be a front side or a back side of the silicon wafer. The impedance test electrodes 425 may include several conductors and or resistors. In some embodiments, the impedance test electrodes are interdigitated electrodes. The measurement may involve application of current and/or voltage and measuring a resulting voltage and/or current. For example, for an impedance test, an impedance spectroscopy may be conducted over a frequency range, for example, between 100 Hz and 10^6 Hz or even higher than mega hertz.

In operation 213, the test fluid is flushed from the integrated electro-microfluidic probe card and the first test area after testing and reading. The flush may include vacuuming, adding a stream of cleaning fluid, for example, deionized water, an inert fluid or gas and drying. The sensing surface may include some bioreceptors that require wetting or other preservation technique to prevent from degradation or detachment.

The method 200 may return to operation 209 and flow a second test fluid different from the first test fluid through the integrated electro-microfluidic probe card to the first test area. In the impedance test example, test fluids having various concentrations of biomolecules may be used in different test loops along with a control fluid. Numerical analysis may be performed on results from different test loops to determine whether the active die associated with the test is accepted.

In some embodiments, instead of flushing and re-flowing a test fluid, some additional test fluid is added to the well. Depending on the test protocol to be performed, a number of test fluids may be used resulting in different numbers of loops. In one example, a pH test protocol may include 4 test fluids: Phosphate buffered saline (PBS), PBS with one portion of hydrochloric acid (HCl), PBS with two portions of HCl, and PBS with three portions of HCl.

After the requisite number of test fluids are flowed, measured, and flushed through the test area, the results are compared against expected ranges and the test area is marked "pass or "not pass" based on the electrical property measurement in operation 219 of method 200. This comparison may be performed separately from the test sequence by a performing numerical analysis using the raw data form operation 211. In some embodiments, the raw data from several test areas may be collected before the analysis is performed. In other embodiments, the wafer-level biosensor testing tool performs the analysis while the test is conducted.

After all the raw data is collected from a test area, the integrated electro-microfluidic probe card is dismounted from the test area on the wafer in operation 221. The dismounting may include reducing the pressure from the manipulator arm and/or the wafer stage against the integrated electro-microfluidic probe card and may also include passing a higher pressure gas through the integrated electro-microfluidic probe card to cause the seal formed in operation 205 to be broken. If the integrated electro-microfluidic probe card has already tested a requisite number of test areas on the biosensor device wafer, then the integrated electro-microfluidic probe card moved to a home position away from the biosensor device wafer. Otherwise, the method 200 repeats from operation 203 where the integrated electro-microfluidic probe card is moved to a separate test area different from the first test area to continue testing the biosensor device wafer by mounting the integrated electro-microfluidic probe card to a different test area on the biosensor device wafer.

In order to accept a biosensor device wafer, a percentage of first specified number of test areas should pass the test. Method 200 includes decision block 223 to determine whether the wafer is "acceptable" or "not acceptable" based on the results from a first specified number of test areas. The test areas may be chosen to have a range of distances from a center of the biosensor device wafer and may be chosen to have different radial angles to cover other process non-uniformity. In one embodiment, a first specified number of test areas may be between about 5 and about 10, and wafer acceptance may require passing of all of the test areas or 80% or better of the test areas.

In some embodiments, the results from the test areas are used to qualify the wafer or dies for different quality bins. A first bin include only those wafers or dies that are accepted based on the first specified number of test areas and a number of bins may be shipped to the customer. In other embodiments, only accepted bins are shipped. If the wafer is accepted in decision block 223, then the wafer is marked pass or "first bin" in operation 229. If the wafer is not accepted in decision block 225, the wafer may be further tested for a second specified number of test areas in operation 225. The additional testing includes performing operations 203 to 221 for each of the second specified number of test areas. In some embodiments, the second specified number of test areas is greater than the first specified number, and the test areas from the entire wafer may be included in the second round of testing. In other embodiments, only new test areas from wafer portions close to the test areas failing the first round of testing are tested. The percentage ratio of passing test areas to accept the wafer using the second specified number of test areas may be greater than the percentage ratio for the first specified number of test areas. In decision block 227, whether the wafer is "acceptable" or "not acceptable" based on the results from a second specified number of test areas is determined. If the wafer is acceptable, then the wafer is marked as pass or "second bin" in operation 231. If the wafer is found to be not accepted, it may be discarded, marked as "failed", or recycled in operation 233.

FIG. 3 shows an example biosensor device wafer having a total of 176 active die locations. Each active die location may include one or more associated test areas. In one example, the first specified number of test areas includes those associated with die 81, 12, 31, 142, and 133 from the center and four quadrants of the wafer 300. If one of the test areas fail the test, for example 133, then other dies within the same quadrant are selected for further testing, for example, 104, 107, 109, 134, 136, 157, 159, 161, and 168. In a second example, the first specified number of test areas includes same dies as the first example, and the second specified number of test areas includes more dies from all quadrants of the wafer. The testing protocol for acceptance of the wafer is specified by a customer prior to wafer fabrication.

Figure 4C:
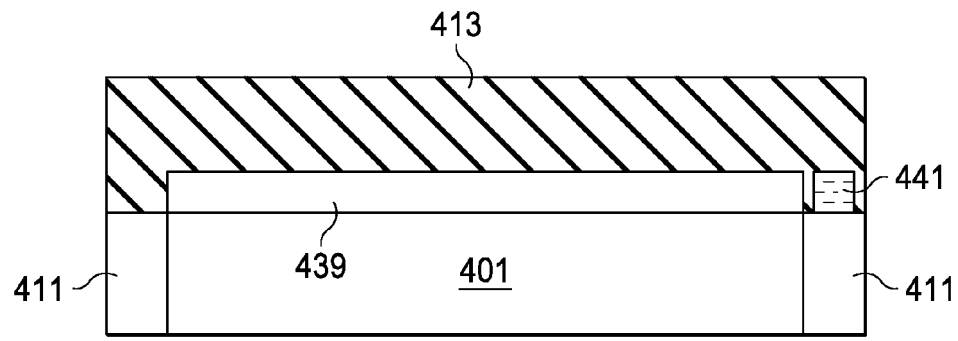

FIGS. 4B to 4E shows various cross sections of the biosensor device die and the integrated electro-microfluidic probe card when mounted. The integrated electro-microfluidic probe card may be designed with a sealed cavity 439 over the active die portion as shown in FIG. 4C, through the sectional view B-B', and FIG. 4D, through the sectional view C-C'. The sealed cavity 439 protects the active die area during testing from contamination by the test fluids or the composition material of the electro microfluidic probe without adding pressure to the fabricated biosensors. FIG. 4C shows the fluidic well 441 over the biosensor 423 in the test area 411. There are no fluidic wells over the scribe line areas 403 and 405 in the cross section view of FIG. 4D.

Figure 4D:
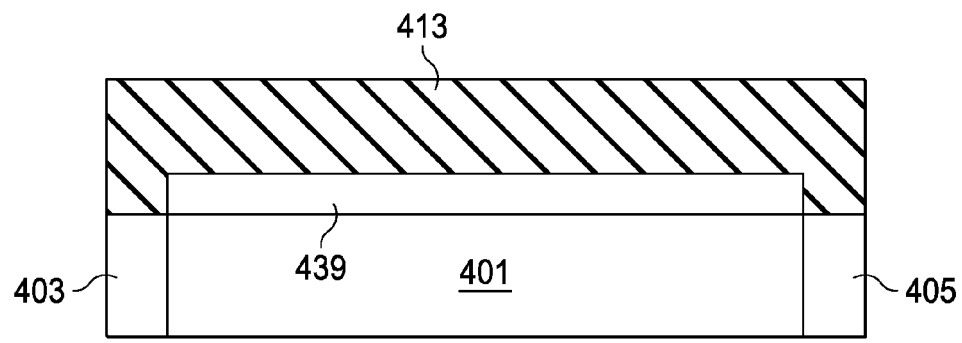
Figure 4E:
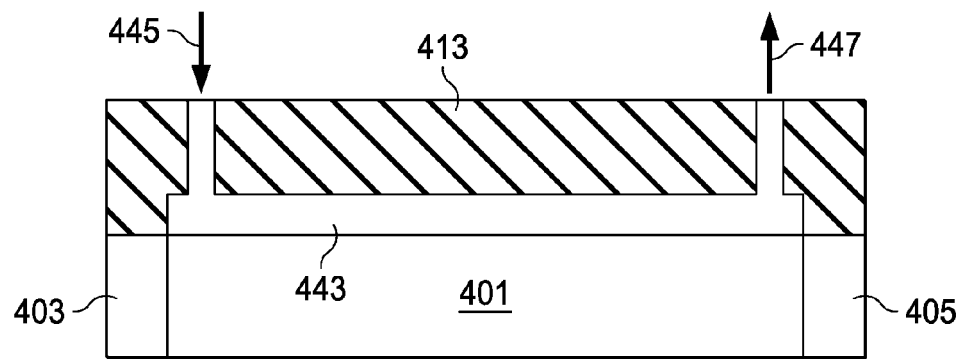

FIG. 4E is an alternative embodiment to the cross section view of FIG. 4D. In this embodiment a fluidic inlet 445 and outlet 447 are formed in the integrated electro-microfluidic probe card cross section. The fluidic inlet 445 and outlet 447 connect to a fluidic cavity 443. This embodiment allows test fluids or process fluids to be added to the fluidic cavity 443 over the active die area. This feature may be useful to test the device performances or process residues as well as perform further analysis after an associated test area fails a test by testing the active die itself. In other embodiments, this feature may be used to add process fluids to preserve or functionalize the sensing surface in the active die area.

Referring back to FIG. 4A, in some embodiments, a test area 409 may be formed within the active die 401. The test area 409 is sealed from the active die 401 to avoid contamination by the test fluid and includes a fluid inlet 435, a fluidic outlet 437, and corresponding electrodes (not shown).

According to various embodiments, the methods and system of the present disclosure may be used to monitor the process performance not only after the biosensor device wafer is completed, but also during manufacturing. For example, impedance spectroscopy may be used to monitor the film quality or the amount of residue. Because each test sequence may use only a number of test areas, even if the test areas are not re-used in subsequent monitoring, a partially fabricated biosensor device wafer may be tested several times. Such process monitoring allows partial re-working on one or more layers of the partially fabricated biosensor device wafer before the wafer acceptance test. In one example, etch residues detected by an impedance spectroscopy may be reduced by wet etching using dilute HF before a different layer is deposited. Similarly, film thickness could be determined by sheet resistance measurement and be increased if it is thinner than target.

In some embodiments, the methods and systems of the present disclosure is used to perform functional tests of devices that replicate, as close as possible, the actual usage of the biosensor devices without rendering a single-use biosensor device un-usable. Such functional testing may include ion-sensitive detection with bioreceptors. Additionally, the methods and systems of the present disclosure may be used to characterize the biosensor devices for customer's information. Such characterization may include capacitance-voltage and current-voltage curves for different analyte concentrations.

One feature of the various embodiments of the present disclosure involves the use of automated electrical testing suitable for mass-manufacturing. Known conventional inspection methods for biosensor device wafers involves manual optical inspections and often includes destructive testing without a chance for reworking. The various embodiments of the present disclosure enable a biosensor foundry to qualify its process and device performance. A biosensor device wafer may be accepted for shipment without time-consuming and expensive external testing.

A variety of biosensors and tests may be performed in the test areas. In addition to the pH sensing and impedance spectroscopy examples discussed, other example tests include DNA sequencing, DNA hybridization, biomolecule immobilization, and biomolecule detection by immune-enzymatic reaction. Biomolecules detected may include protein, virus, bacteria, cells, and parts of each of these.

After a biosensor device wafer is accepted, the wafer may be diced (singulated) into individual biochips and prepared for shipment. The singulation occurs on the scribe lines, which may be about 80 microns wide, and may destroy the test areas. In some embodiments, one or more fluidic substrates is bonded to the biosensor device wafer before the singulation. The biochips may be further packaged into a device assembly at the biosensor foundry, a packaging house, or the customer.

One aspect of the present disclosure pertains to a method for testing a biosensor device wafer having a plurality of test areas, the method comprising: aligning the biosensor device wafer on a wafer stage of a wafer-level biosensor testing tool; mounting an integrated electro-microfluidic probe to a first test area on the biosensor device wafer; creating a seal between fluidic probes on the integrated electro-microfluidic probe card and the first test area; electrically connecting one or more electronic probe tips on the integrated electro-microfluidic probe card to conductive areas of the first test area; flowing a test fluid from a fluid supply through the integrated electro-microfluidic probe card to the first test area; and, electrically measuring via the one or more electronic probe tips one or more electrical properties of one or more devices in the first test area that is exposed to the test fluid. The one or more electrical properties include one or more of impedance spectroscopy, pH level, current versus voltage curve, and capacitance versus voltage curve.

In some embodiments, the method further includes flushing the test fluid from the integrated electro-microfluidic probe and the first test area; flowing a second test fluid from the fluid supply through the integrated electro-microfluidic probe card to the first test area; and, electrically measuring via the one or more electronic probe tips the one or more electrical properties. The method may also include marking the first test area either as "pass" or "not pass" based on the electrical property measurement; dismounting the integrated electro-microfluidic probe card from the first test area on the wafer; mounting the integrated electro-microfluidic probe card to a second test area on the wafer; and repeating the flowing and the electrical measuring operations.

In another aspect, the present disclosure pertains to a biosensor device wafer that includes a plurality of device areas separated from each other by scribe lines, and at least one test area associated with each of the plurality of device areas. Each test area includes at least one fluid channel, one fluid input, one fluid output, at least one biosensor, and electrodes.

In yet another aspect, the present disclosure pertains to an integrated electro-microfluidic probe card that includes a fluidic mount, at least one microfluidic probe and a plurality of electronic probe tips disposed on the first major surface in the testing portion of the fluidic mount, at least one fluidic input and at least one fluidic output on one or more minor surfaces of the fluidic mount, an input/output electronic port on the fluidic mount electrically coupled to the plurality of electronic probe tips, and one or more handle lugs attached to the fluidic mount. The fluidic mount includes a plurality of microfluidic channels in one or more testing portion of the fluidic mount. The fluidic mount may include a device portion that is not in fluidic communication with the test portion.

In describing one or more of these embodiments, the present disclosure may offer several advantages over prior art devices. In the discussion of the advantages or benefits it should be noted that these benefits and/or results may be present is some embodiments, but are not required in every embodiment. Further, it is understood that different embodiments disclosed herein offer different features and advantages, and that various changes, substitutions and alterations may be made without departing from the spirit and scope of the present disclosure.

What is claimed is:

1. A method for testing a biosensor device wafer having a plurality of test areas, the method comprising:
   aligning the biosensor device wafer on a wafer stage of a wafer-level biosensor testing tool;
   mounting an integrated electro-microfluidic probe card to a first test area on the biosensor device wafer;
   creating a seal between fluidic probes on the integrated electro-microfluidic probe card and the first test area;
   electrically connecting one or more electronic probe tips on the integrated electro-microfluidic probe card to conductive areas of the first test area;
   flowing a test fluid from a fluid supply through the integrated electro-microfluidic probe card to the first test area; and,
   electrically measuring via the one or more electronic probe tips one or more electrical properties of one or more devices in the first test area that is exposed to the test fluid.

2. The method of claim 1, further comprising:
   flushing the test fluid from the integrated electro-microfluidic probe card and the first test area;
   flowing a second test fluid from the fluid supply through the integrated electro-microfluidic probe card to the first test area; and electrically measuring via the one or more electronic probe tips the one or more electrical properties.

3. The method of claim 2, wherein the second test fluid comprises the test fluid and hydrochloric acid.

4. The method of claim 1, wherein the test fluid is de-ionized water.

5. The method of claim 1, wherein the test fluid is phosphate buffered saline.

6. The method of claim 1, wherein the plurality of test areas is within a scribe line.

7. The method of claim 1, wherein the plurality of test areas include test areas in a device area and test areas within a scribe line.

8. The method of claim 7, wherein the one or more devices comprises a backside sensing biological field-effect-transistor (bioFET) or interdigitated electrodes.

9. The method of claim 1, further comprising:
marking the first test area either as "pass" or "not pass" based on the electrical property measurements;
dismounting the integrated electro-microfluidic probe card from the first test area on the biosensor device wafer;
mounting the integrated electro-microfluidic probe card to a second test area on the biosensor device wafer; and
repeating the flowing and the electrical measuring operations.

10. The method of claim 1, further comprising:
repeating the mounting, creating a seal, electrically connecting, flowing, and electrically measuring operations for a first specified number of test areas; and
marking the biosensor device wafer as "acceptable" or "not acceptable" based on the electrical property measurements for the first specified number of test areas.

11. The method of claim 10, further comprising:
if the biosensor device wafer is "not acceptable", repeating the mounting, creating a seal, electrically connecting, flowing, and electrically measuring operations for a second specified number of test areas; and
marking the biosensor device wafer as "acceptable" or "not acceptable" based on the electrical property measurements for the second specified number of test areas; and
wherein the second specified number of test areas is at least one order of magnitude greater than the first specified number of test areas.

12. The method of claim 10, further comprising:
if the biosensor device wafer is "not acceptable", repeating the mounting, creating a seal, electrically connecting, flowing, and electrically measuring operations for a second specified number of test areas; and
marking a bin level for the biosensor device wafer based on the electrical property measurements for the second specified number of test areas; and
wherein the second specified number of test areas is at least one order of magnitude greater than the first specified number of test areas.

13. The method of claim 1, wherein the one or more electrical properties includes one or more of impedance spectroscopy, pH level, current versus voltage curve, and capacitance versus voltage curve.

14. A biosensor device wafer comprising:
a plurality of device areas separated from each other by scribe lines;
each of the plurality of device areas comprising an active region, wherein each active region includes at least one operational biosensor; and
at least one test area associated with each of the plurality of device areas, the at least one test area associated with each of the plurality of device areas being within the scribe line adjacent to each of the plurality of device areas, wherein each test area includes at least one fluid channel, one fluid input, one fluid output, at least one biosensor, and electrodes.

15. The biosensor device wafer of claim 14, further comprising at least one active region test area associated with each of the plurality of device areas, the at least one active region test area being within each of the device areas.

16. The biosensor device wafer of claim 14, wherein the at least one biosensor comprises a BioFET or interdigitated electrodes.

17. The biosensor device wafer of claim 14, wherein the at least one test area associated with each of the plurality of device areas comprises a plurality of test areas associated with each of the plurality of device areas.

18. An apparatus, comprising:
a fluidic mount having a bottom surface and a top surface and at least one side surface, the fluidic mount having at least one fluidic input and at least one fluidic output and at least one microfluidic probe disposed on the bottom surface of the fluidic mount;
the fluidic mount further including a plurality of electronic probe tips disposed on the bottom surface of the fluidic mount, the electronic probe tips coupled to an input/output electronic port on the fluidic mount;
the at least one microfluidic probe configured to form a seal around at least one microchannel located in a test area for a biological field-effect transistor (bioFET), wherein the test area is disposed on a biochip wafer; and
the plurality of electronic probe tips configured to contact at least one conductive area of a test area for a bioFET.

19. The apparatus of claim 18, further comprising:
at least one manipulator arm attached to at least one of the top surface or the at least one side surface of the fluidic mount.

20. The apparatus of claim 18, further comprising:
at least one fluid supply reservoir and tube attached to the at least one fluidic input; and
at least one fluid return reservoir and tube attached to the at least one fluidic output.

21. The apparatus of claim 18, further comprising:
at least one light source external to the fluidic mount and proximate to at least one of the bottom surface or the top surface of the fluidic mount; and
an optical detector external to the fluidic mount and proximate to at least one of the bottom surface or the top surface of the fluidic mount.

* * * * *